United States Patent [19]
Griffel, Jr. et al.

[11] Patent Number: 5,360,823
[45] Date of Patent: Nov. 1, 1994

[54] ANIONIC SALT FORMULATION FOR MILK FEVER

[75] Inventors: Gilbert W. Griffel, Jr., Fort Dodge, Iowa; David J. Kirk, Mukwonago, Wis.

[73] Assignee: Dawe's Inc., Chicago, Ill.

[21] Appl. No.: 146,983

[22] Filed: Nov. 2, 1993

[51] Int. Cl.$^5$ .................... A01N 31/00; A01N 59/02
[52] U.S. Cl. .................... 514/706; 514/740; 424/705; 424/719
[58] Field of Search ................. 514/706; 424/705, 719

[56] References Cited

U.S. PATENT DOCUMENTS

| | | | |
|---|---|---|---|
| 2,927,859 | 3/1960 | Gordon | 99/4 |
| 3,873,728 | 3/1975 | Moore | 426/2 |
| 4,452,779 | 6/1984 | Cockerill | 424/128 |
| 4,479,978 | 10/1984 | Robertiello et al. | 426/636 |
| 4,988,520 | 1/1991 | Overton | 426/74 |
| 4,996,065 | 2/1991 | Van De Walle | 426/72 |
| 5,064,665 | 11/1991 | Klopfenstein et al. | 426/2 |
| 5,204,102 | 4/1993 | Coles et al. | 424/195.1 |
| 5,219,596 | 6/1993 | Smith et al. | 426/2 |
| 5,232,698 | 8/1993 | Hord | 424/195.1 |

OTHER PUBLICATIONS

Wang C. et al. J. Dairy Sci (Mar. 1992) 75(3).
van de Braak AG et al Vet O (Jan. 1986) 8(1) 24–37.
Block. E. J. Dairy Sci (Dec. 1984) 67(12) 2939–48.
Beede, Feed Management, vol. 43, No. 6, Jun. 1992, pp. 28, 30, 31.
West, Feedstuffs, May 10, 1993, pp. 14, 15, 22.
Goff et al., "Anionic salts help prevent milk fever", Dec. 1992, p. 837.
Central Soya Feed Company Brochure, "MasterMix Dry Cow Supplements", 1992.
Purina Mills, Inc. Brochure, "Dry Cow Feeding and Management Program", 1992.
Farmland Industries, Inc. Brochure, "Anionic Dry Cow Diets" 1992.
Frontiers in Nutrition, No. 316 "Dietary Cation-Anion Balance", as reported at 85th Annual American Dairy Science Assoc. Meeting, Jun. 24–27, 1990 p. 3.
Frontiers in Nutrition, No. 321, "Dietary Cation-Anion Difference: A Review", as reported at 88th Annual American Dairy Science Assoc. Meeting, Jun. 13–16, 1993, p. 6.

*Primary Examiner*—Paul J. Killos
*Attorney, Agent, or Firm*—Zarley, McKee, Thomte, Voorhees & Sease

[57] ABSTRACT

A treatment method and composition for milk fever prevention in dairy cows. The method involves administering to a dry cow prior to freshening a calcium mobilizing anionic salt feed additive that is substantially free of ammonium salts.

15 Claims, No Drawings

ANIONIC SALT FORMULATION FOR MILK FEVER

BACKGROUND OF THE INVENTION

Milk fever is a metabolic disease occurring soon after freshening (calving) in cows. It is characterized by a drastically decreased calcium concentration in the blood. As a result of hypocalcemia (low blood ionized calcium concentrations), the cow may lose muscle tone, making her unable to stand or rise. It is known that milk fever can be effectively treated through intravenous administration of calcium gluconate, but it is also known that cows, once having suffered milk fever, have economic losses in terms of their overall health, effective yield of milk, susceptibility to other disease complexes such as Ketosis, Displaced Abomasum, Retained Placenta, increased susceptibility to Mastitis, etc.

It has been discovered that milk fever can be effectively treated and/or prevented by feeding dairy cows during the close up period (14 to 21 days pre-calving) a diet containing substantial amounts of negative ions (i.e., anionic salts). See Beede, *Feed Management*, Jun. 1992, Vol. 93 No. 6 pp.28-31. While it is not known precisely why an anionic diet works to effectively prevent milk fever, it is theorized that in order to physiologically neutralize the negative charged diet, a reduction in blood PH occurs which increases mobilization of bone calcium. Therefore, at parturition the potential for hypocalcemia is reduced because the pathways for calcium reabsorption from the bone are active. As Dr. Beede states in his article, the exact mechanism by which a negative cation-anion balance (here described as dietary cation-anion difference (DCAD)) influences metabolism in dairy cattle is unclear. Nevertheless, the end result of feeding anionic salt feed additive is that blood calcium concentrations are maintained near normal and the metabolic machinery to increase blood calcium is readily functionalized. This situation can be immensely helpful to the pre-partum cow.

As a result of the above-described knowledge, many in the feed industry have developed anionic salt feed additives that are promoted for feeding to a dry cow prior to freshening. The typical salt treatments as now commercially available contain substantial amounts of sulfate ions and of ammonium chloride and ammonium sulfate with the conventional thinking that since chloride and sulfate are essential and since ammonium is a weak cation, the use of these salts will favor a negative or anionic balance. While indeed they do favor a negative or anionic balance, these products are not found palatable by the cows. The high amount of sulfate anion and ammonia make the product unpalatable. As a result, when free choice fed to animals, despite the fact that the composition has the ability to help the cow, the composition is not very effective because the animal simply will not eat them due to their unpalatable nature.

In the past elemental sulfur has been disregarded as a potential source of needed sulfur because early in vitro research indicated poor availability of elemental sulfur for bacterial fermentation. However, in the combination of this invention elemental sulfur, which is more concentrated than sulfate, is bioavailable and is after ingestion converted to bioavailable format.

Accordingly, it is a primary objective of the present invention to prepare an effective anionic feed additive which has the proper cation-anion balance (DCAD) but which is also highly palatable and has significantly reduced levels of ammonium salt additives and which uses free sulfur as a sulfate source.

Another objective of the present invention is to provide a method of preventative treatment for milk fever comprising administering to a dry cow a small but calcium mobilizing effective amount of an anionic salt feed additive that is of significantly reduced levels of ammonium salts and which contains elemental sulfur as opposed to sulfate as the predominant sulfur source.

Another objective of the present invention is to provide a preventative treatment feed additive DCAD balanced composition which will achieve the above-described results.

Another objective of the present invention is to provide a composition which can be effectively and economically produced, a composition which can be pelletized and if desired free choice fed either alone or as part of a total mixed feed ration, and a composition which the cattle themselves regard as highly palatable.

The method and means of accomplishing the above objectives as well as others will become apparent from the detailed description of the invention which follows hereinafter.

SUMMARY OF THE INVENTION

A method of treatment for milk fever and a palatable composition for the same is provided. The method comprises administering to a dry cow from 14 to 21 days prior to calving a calcium mobilizing effective amount of an anionic salt feed additive to achieve a cation-anion balance in the total dry matter diet within the range of from $-8$ to about $-18$. The composition is of reduced ammonium salt additives and contains substantial amounts of elemental sulfur to replace sulfate as well.

DETAILED DESCRIPTION OF THE INVENTION

Anionic salts act to lower the dietary cation-anion difference (DCAD) of the diet. Cation-anion difference is calculated as follows. Here mEq is the abbreviation for "milliequivalents". This is used as a measure of osmotic and electrical activity of these nutrients. Diets with a positive DCAD are considered alkaline and cationic, while those with a negative DCAD are acidic and anionic. Anionic diets have been demonstrated to reduce the incidence of milk fever, while cationic diets can increase cases of milk fever. Anionic diets prevent milk fever by increasing the release of calcium stored in the bone, and triggering the activation of Vitamin $D_3$—all of which help the cow respond to the great increase in calcium demand at calving. In its most complete form the cation-anion balance (DCAD) is expressed in milliequivalents (mEq) of salt per hundred grams of dry matter.

Using the above-described formula which is explained in more detail in the Beede reference above referred to, it has been discovered that the feed additive should be used to provide a cation-anion difference in the total diet within the range of from $-8$ to about $-18$, preferably from about $-10$ to about $-15$. When the anionic feed additive has a DCAD within the negative range on a per lb. basis of $-2000$ mEq to $-3500$ mEq, it will function effectively as a milk fever preventative and provide the above-mentioned DCAD balance.

The timing of feeding of the anionic feed additives as hereinafter described can roughly be referred to as during the transition period. This period refers to from about 14 to 21 days prior to calving up to the calving period. During this time dry cows are shifted from a low energy, high fiber cow diet to a diet containing intermediate levels of concentrates. As a result, the cow is readied for the significantly increased demand that will occur after calving. It is during this time frame that an anionic salt feed additive will, if properly ingested, mobilize the calcium metabolism pathways, readying the animal for the huge calcium demands that occur during milk production.

After much time developing and formulating anionic feed additives, including field observations, gathering data from actual dairy herds, etc., it has been discovered that many dairy farmers are totally unsatisfied with the current commercial anionic salt feed additives, blaming them as ineffective when in fact scientific results have proven them quite effective. Observations of the herds themselves have revealed the problem is that they do not like anionic salt feed additives and prefer to avoid eating them whenever possible. This occurs despite various attempts at heavy masking of unpalatable flavors and odors with conventional flavorants, top dressings such as cane molasses, etc. This invention provides a palatable product.

In accordance with the present invention, it has been discovered that one of the primary reasons for the animals' dislike of anionic salt feed additives is the high level of ammonium salts typically added in the form of ammonium chloride and ammonium sulfate. While the addition of these provides the requisite DCAD balance required for milk fever preventative, it does little good to have a nutritional supplement properly balanced to provide a benefit if the animal will not eat it.

In accordance with the present invention, the proper cation balance as above-described is provided in a system that is of reduced ammonium salts and which uses elemental sulfur as a primary sulfur source. It also provides higher amounts of palatable additives such as distillers dried grain with solubles, wheat midds, etc.

As earlier explained, the cation-anion difference of the total diet should be within the range of from about −8 to about −18, preferably from about −10 to about −15. The amount of the composition fed should be an amount sufficient to supply at least −2000 mEq to −3500 mEq per lb. per cow daily DCAD.

The composition does not have to be completely free of ammonium salts but needs to be of reduced level of ammonium salts. Thus having these salts present is alright if only at such a level that their unpalatable nature can easily be masked by flavorants at commonly added flavor levels. Preferably, sulfate salt should not be more than about 15% of the composition and ammonium salt should not be more than about 10% of the composition. Elemental sulfur can be added at from 1.25% to 7.5% by wt.

The composition of the present invention can be fed free choice, as a top dressing, but is preferably pelletized and fed as part of a total feed ration, with the amount employed in the total feed ration calculated to provide about one pound of anionic salt feed additive per cow per day. When cows consume approximately a pound per day minimum, they provide a sufficient amount of anionic salt in their total dry matter diet to promote calcium mobilization and to provide each cow on a per cow basis the desired DCAD. Care should be taken to not exceed the levels expressed herein, i.e. about 1 lb./animal per day because too much can cause acidosis. The important amount required is an amount to simply open the calcium metabolic pathways and ready them for the demand which occurs during milk production.

A wide variety of salts used for mineral supplementation can be used in the anionic salt feed additives of the present invention as long as they are substantially free of ammonium ions, they preferably contain elemental sulfur, and they provide a palatable composition with a DCAD within the range previously expressed. Preferably the composition can include from about 5% to about 25% distillers dried grains with solubles, from about 25% to about 45% wheat midds, from about 2.5% to about 10% cane molasses, and from about 5% to about 10% calcium sulfate. Additionally, other ingredients expressed here as minors can be included such as flavor additives, traditional trace mineral supplements for zinc, iron, etc., and of course sufficient levels of vitamins A, D and E to provide the recommended daily allowances.

Some typical examples of formulas useful to achieve the results of this invention include the following listed formulas.

TABLE 1

| INGREDIENT | FORMULA ONE | FORMULA TWO | FORMULA THREE |
|---|---|---|---|
| Wheat Midds | 723.5 | 1033.5 | 861.5 |
| Ammonium Chloride | 280.0 | 160.0 | 250.0 |
| Magnesium Sulfate | 200.0 | 100.0 | 140.0 |
| Calcium Sulfate | 200.0 | 100.0 | 200.0 |
| Dist. Dried Grains w/Solubles | 200.0 | 200.0 | 200.0 |
| Cane Molasses | 100.0 | 100.0 | 100.0 |
| Ammonium Sulfate | 100.0 | 10.0 | 2.0 |
| Trace Mineral Supplement | 80.0 | 80.0 | 80.0 |
| Animal Fat | 50.0 | 50.0 | 50.0 |
| Sulfur | 50.0 | 150.0 | 100.0 |
| Vitamin E 125,000 | 11.5 | 11.5 | 11.5 |
| Flavor | 2.0 | 2.0 | 2.0 |
| Calcium Chloride | 2.0 | 2.0 | 2.0 |
| Vitamin A 310 | 0.8 | 0.8 | 0.8 |
| Vitamin D3 181.6 | 0.2 | 0.2 | 0.1 |

The following examples are offered to illustrate but not limit both the process and the product of the present invention.

EXAMPLES

A composition on a percent weight basis was prepared in accordance with the following formulation:

| INGREDIENT | % BY WEIGHT | AMOUNT |
|---|---|---|
| Distillers dried grains with solubles | 10.00 | 200.0 |
| Wheat Midds | 42.00 | 853.5 |
| Sulfur | 5.00 | 100.0 |
| Magnesium Sulfate | 10.00 | 200.0 |
| Ammonium Chloride | 9.50 | 190.0 |
| Ammonium Sulfate | .50 | 10.0 |
| Animal Fat | 2.50 | 50.0 |
| Trace Mineral Supplement | 4.00 | 80.0 |
| Vitamin E 125 | 5.75 | 11.5 |
| Licorice flavor | .05 | 1.0 |
| Ginger flavor | .05 | 1.0 |
| Vitamin A 310 | .04 | .8 |
| Vitamin D3 181.6 | .01 | .2 |
| Cane Molasses | 5.00 | 100.0 |
| Calcium Sulfate | 5.00 | 200.0 |
| Calcium Chloride | .10 | 2.0 |

The guaranteed analysis per pound of the above product was as follows:

| | |
|---|---|
| Protein, Min. % (Contains 16.00% Crude Protein from Non-Protein Nitrogen) | 25.00 |
| Fat, Min. % | 3.00 |
| Fiber, Max. % | 6.00 |
| Iodine, % | 0.002 |
| Vitamin A, I.U. | 200,000 |
| Vitamin D. I.U. | 50,000 |
| Vitamin E. I.U. | 1,000 |
| Selenium, % | 0.00077 (3.50 mg/lb) |

Pelletized, this product was fed to dairy cows for 21 days prior to the expected calving date at a rate of one pound per cow per day. This level provided that the cows would receive at least 100 grams of calcium as part of their daily dry matter intake.

The above formulation, free choice fed in pelletized fashion, was provided to dairymen and their results of use observed. In every instance dairymen reported that the cows fed the above formulation calved and cleaned faster; had little or no incidence of milk fever; and also observed much less of other disease complexes such as Ketosis or Displaced Abomasums after calving. The cows also were noticed to reach peak milk production sooner and to maintain this high milk production for longer periods of time.

Feed Acceptance Test

In another example this same above-described formulation of the product of the present invention, referred to in the below table as CLOSE-UP TM pellet, was compared with a conventional anion salt additive sold by VITAPLUS TM under the mark ACID-I-FRESH TM in feedings observed by one veterinarian and a dairy producer. These were done on two separate farms with the observations recorded as indicated in Table II below.

TABLE II

| COW # | FEED ACCEPTANCE TEST PREFERENCE RESULTS |
|---|---|
| | FARM 1 |
| Cow #93 | Consumed both pellets equally well. Showed no clear preference for either. |
| Cow #91 | Consumed the CLOSE-UP PELLET. Refused the ACID-I-FRESH pellet. |
| Cow #102 | Consumed both pellets equally well. Showed no clear preference for either. |
| Cow #100 | Consumed the CLOSE-UP PELLET. Refused the ACID-I-FRESH pellet completely. |
| Cow #49 | Consumed the CLOSE-UP PELLET first. Consumed the ACID-I-FRESH pellet second. |
| Cow #45 | Consumed both pellets equally well. Showed no clear preference for either. |
| Cow #120 | Refused both pellets completely. |
| Cow #125 | Consumed the CLOSE-UP PELLET. Refused the ACID-I-FRESH pellet completely. |
| Cow #101 | Consumed the CLOSE-UP PELLET. Refused the ACID-I-FRESH pellet completely. |
| | FARM 2 |
| Cow #1 | Consumed CLOSE-UP PELLET. Totally refused ACID-I-FRESH. |
| Cow #2 | Consumed CLOSE-UP PELLET. Totally refused ACID-I-FRESH. |
| Cow #3 | Consumed CLOSE-UP PELLET. Totally refused ACID-I-FRESH. |
| Cow #4 | Consumed CLOSE-UP PELLET. Totally refused ACID-I-FRESH. |
| Cow #5 | Refused both products completely. |
| Cow #6 | Tasted ACID-I-FRESH, then consumed CLOSE-UP PELLET completely. Did not consume any more ACID-I-FRESH. |
| Cow #7 | Consumed CLOSE-UP PELLET. Totally refused ACID-I-FRESH. |
| Cow #8 | Refused both products completely. |
| Cow #9 | Consumed both products completely with no clear preference. |
| Cow #10 | Consumed both products completely with no clear preference. |

As seen from Table II above in the Feed Acceptance Test, 11 out of the 19 cows showed a distinct preference for the composition of the present invention. The composition of VITAPLUS, ACID-I-FRESH was a conventional anionic salt composition that contained substantial amounts of ammonium salts and did not contain free sulfur but instead contained substantial amounts of sulphate anion. A preference of 11/19ths or 58.4% is significant, especially when considering that cows that showed no particular preference in an initial feeding were not followed up or counted as positive results in the acceptance test calculation. This is even more impressive when considering that the ACID-I-FRESH pellet is recommended to be fed at a rate of 1.25 lbs. per day per head and therefore is recommended at a higher feed rate than the CLOSE-UP PELLET. In the testing both products were placed simultaneously side-by-side in front of each individual cow held in a stanchion barn.

What is claimed is:

1. A method of preventative treatment for milk fever; comprising:
   administering to a dry cow prior to freshening a small but calcium mobilizing effective amount of an anionic salt feed additive to provide a cation-anion difference (DCAD) in the total dry matter diet within the range of from about −8 to about −18, said anionic salt additive being of reduced levels of ammonium salts and containing elemental sulfur.

2. The method of claim 1 wherein the DCAD is within the range of from about −10 to about −15.

3. The method of claim 1 wherein the anionic salt additive includes elemental sulfur as a primary source of dietary sulfate.

4. The method of claim 3 wherein the anionic salt additive includes distillers dried grain with solubles, wheat middlings and cane molasses.

5. The method of claim 1 wherein the administration is in the form of a pelletized feed additive to a total mixed feed ration.

6. The method of claim 1 wherein the administering begins from 14 to 21 days prior to freshening.

7. The method of claim 2 wherein the amount of anionic salt feed additive is sufficient to supply at least −2000 to −3500 mEq DCAD per pound per cow daily.

8. The method of claim 7 wherein the anionic salt feed additive contains elemental sulfur as a sulfate source.

9. The method of claim 1 wherein each cow is administered about 1 lb./day of said anionic salt feed additive.

10. A preventative treating composition for milk fever comprising:
    a small but calcium mobilizing effective amount of an anionic feed additive having a cationic-anionic balance within the range of from −8 to about −18, and having from about 1.25% to about 7.5% by weight elemental sulfur.

11. The composition of claim 10 which has a DCAD of from −2000 to −3500 mEq.

12. The composition of claim 11 wherein the composition is in pelletized form.

13. The composition of claim 10 which includes from 5% to 25% distillers dried grains with solubles, from 25% to 45% wheat midds, from 2.5% to 10% cane molasses and from 5% to 10% calcium sulfate.

14. The composition of claim 13 which includes as minors, amounts of flavor additives.

15. The composition of claim 14 which includes a recommended daily allowance of vitamins A, D, E and a trace mineral supplement.

* * * * *